United States Patent [19]
Eriksson et al.

[11] Patent Number: 5,810,324
[45] Date of Patent: Sep. 22, 1998

[54] FLOW REGULATOR WITH TWO SOLENOIDS

[75] Inventors: Per-Göran Eriksson, Täby; Erik Krahbichler, Haninge; Bruno Slettenmark, Järfälla, all of Sweden

[73] Assignee: Siemens-Elema AB, Solna, Sweden

[21] Appl. No.: 919,280

[22] Filed: Aug. 28, 1997

[30] Foreign Application Priority Data

Aug. 30, 1996 [SE] Sweden ................................. 9603160

[51] Int. Cl.⁶ ....................................................... F16K 7/04
[52] U.S. Cl. ........................ 251/7; 251/129.09; 251/129.1
[58] Field of Search ............................... 251/4, 7, 129.09, 251/129.1, 129.19

[56] References Cited

U.S. PATENT DOCUMENTS

| | | | |
|---|---|---|---|
| 1,097,143 | 5/1914 | Singleton | 251/129.09 |
| 4,496,133 | 1/1985 | Sule | 251/7 |
| 4,624,282 | 11/1986 | Fargo | 251/129.1 |
| 4,664,355 | 5/1987 | Kubach | 251/129.09 |
| 4,684,102 | 8/1987 | Dykstra. | |
| 4,972,996 | 11/1990 | Cerny | 251/129.1 |

FOREIGN PATENT DOCUMENTS

| | | | |
|---|---|---|---|
| 0 107 445 | 5/1984 | European Pat. Off. . | |
| 224224 | 11/1968 | U.S.S.R. | 251/7 |
| WO 95/33151 | 12/1995 | WIPO . | |

OTHER PUBLICATIONS

Manual for Siemens Servo Ventilator 300, pp. 136–137 (May 1993).

*Primary Examiner*—Denise L. Ferensic
*Assistant Examiner*—John Ball
*Attorney, Agent, or Firm*—Hill & Simpson

[57] ABSTRACT

A flow regulator, suitable for use in a respirator/ventilator, has a conduit through which a medium flows whose flow is to be regulated and a choke valve arranged outside the conduit. The choke valve includes a first solenoid, a pressure actuator that is moved by the shaft end of the first solenoid, and a fixed element with the conduit disposed between the pressure actuator and the fixed element. Actuation of the first solenoid displaces the pressure actuator so as to alter the cross-section of the conduit. The shaft of the first solenoid exhibits an effective stroke length so that the pressure actuator, in a first limit position, leaves the flow cross-section of the conduit unaltered and, in a second limit position, partially compresses the conduit against the detent. The flow regulator is made lightweight and inexpensive and also has a comparatively low power consumption by using a second solenoid having a shaft which exhibits a short effective stroke length compared to the shaft of the first solenoid. In the end position shaft of the second solenoid exerts a pressure against the pressure actuator so as to compress the conduit further than the compression produced by the first solenoid and thereby to entirely suppress the flow.

8 Claims, 3 Drawing Sheets

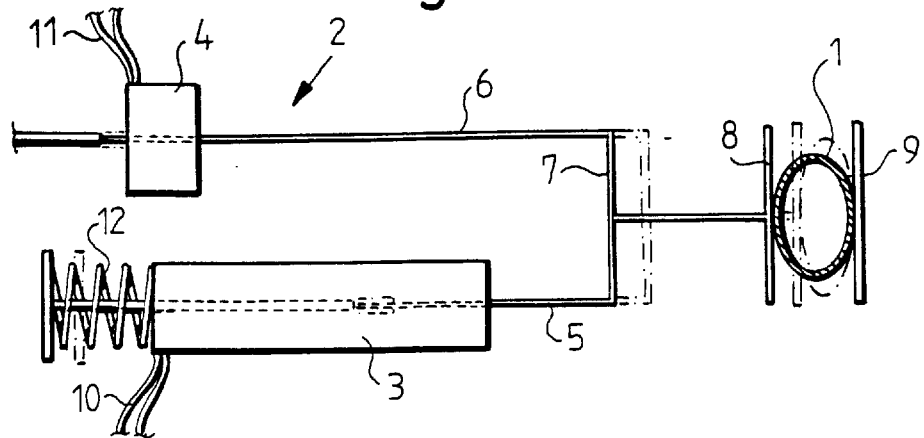
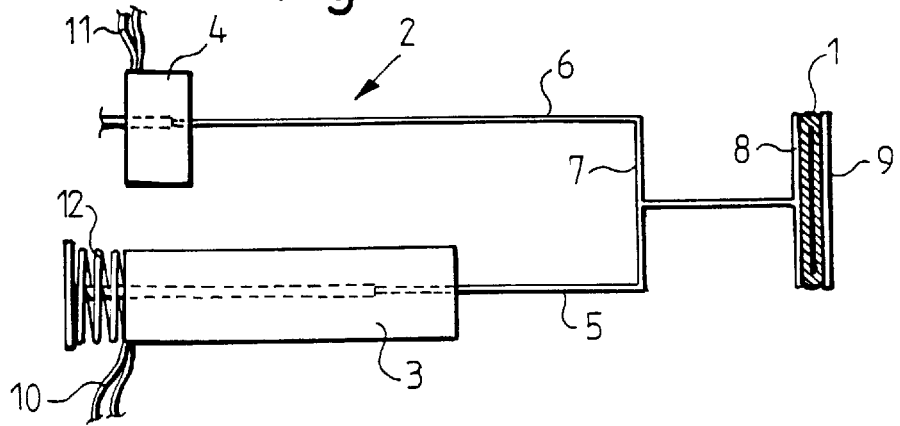
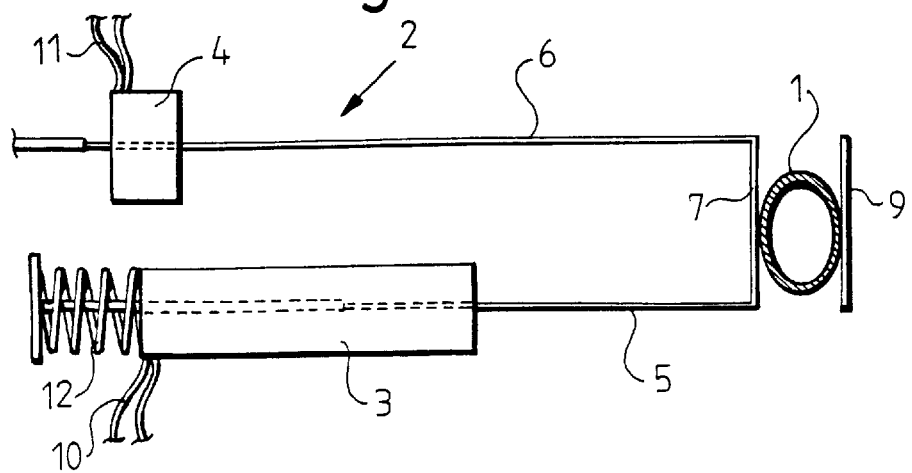

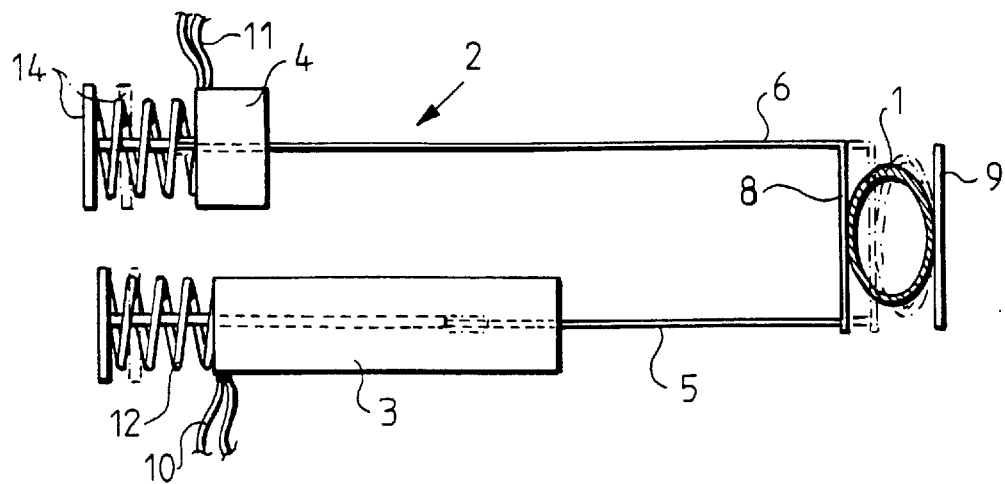
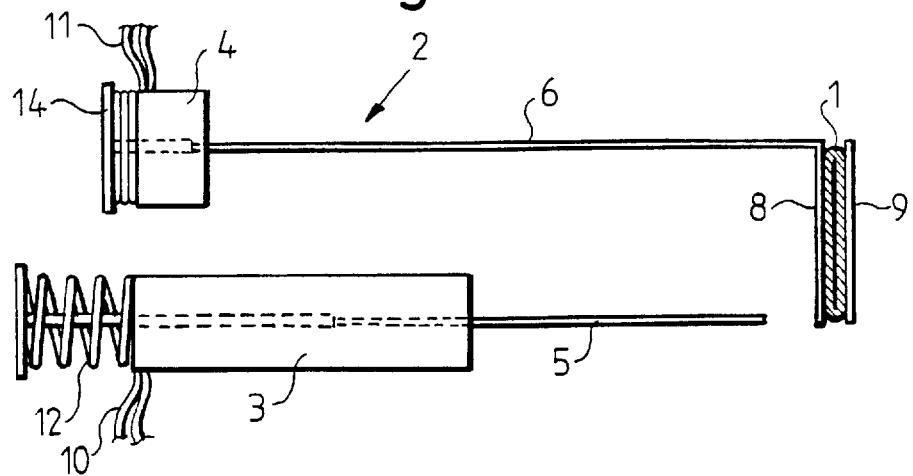

FLOW REGULATOR WITH TWO SOLENOIDS

BACKGROUND OF THE INVENTION

1. Field of the Invention

The invention is directed to a flow regulator suitable for use in a respirator/ventilator.

2. Description of the Prior Art

A flow regulator is known having a compressible conduit through which a medium whose flow is to be regulated flows, a choke valve arranged outside the conduit that includes a first solenoid and a pressure actuator that is moved by the shaft end of the solenoid toward a fixed element for altering the flow cross-section of the conduit, which is disposed between the pressure actuator and the fixed element. The shaft of the solenoid has an effective stroke length such that the pressure actuator leaves the flow cross-section of the conduit unaltered in a first limit position and compresses the conduit against the fixed element in a second limit position.

A flow regulator of this type is shown in the Siemens manual "Servo Ventilator 300" and is provided for controlling the gas flow through the expiration line of a respirator/ventilator during the exhalation phase. During an inspiration phase, the conduit is compressed against the fixed element that the gas flow is entirely suppressed. Since the solenoid is provided not only for controlling the flow cross-section of the conduit but also to completely compress the conduit against the fixed element during about half the operating time, a solenoid is required whose shaft, and the pressure actuator at the end thereof, can exert a disproportionately large force against the conduit at the end of the motion. A solenoid having such properties is expensive, comparatively large and also heavy. Moreover, a solenoid of this type requires a relatively high current during a significant portion of its operating time, this being disadvantageous, especially in cases wherein the respirator/ventilator is battery operated.

SUMMARY OF THE INVENTION

An object of the invention is to provide a flow regulator of the type initially described but having a choke valve that is comparatively light and inexpensive and that also has a comparatively low power consumption.

This object is inventively achieved in a flow regulator of the above type provided with a second solenoid, whose shaft exhibits a shorter effective stroke length compared to the shaft of the first solenoid, which is able to exert a pressure against the pressure actuator in one limit position so that it compresses the conduit further than the compression produced by the first solenoid, and thereby entirely suppresses the flow. Such a solenoid having a comparatively short effective stroke length of about 1 to 2 mm is usually rather small and lightweight but can exert a great force over this short path. As used herein "effective stroke length" means the distance through which the shaft of the solenoid actively moves. The use of the second solenoid allows a solenoid to be employed as the first solenoid which is weaker, and thus smaller and lighter, compared to the known single solenoid, because the shaft thereof need only produce a force sufficient to control the flow cross-section but not to entirely compress the conduit. Even though using two solenoids choke valve is thus established that is lighter in weight and that has a lower power consumption compared to known single-solenoid regulators.

Solenoids suitable for use as the second solenoid are shown and described in the handbook "Solenoids Design Manual" of Shindengen Electric Mfg. Co., Ltd.

In an embodiment of the invention the second solenoid is dimensioned such that it can generate a force against the conduit that itself can completely compress the conduit against the detent. This allows the current for the first solenoid to be shut off when the conduit is completely compressed against the fixed element. An extremely low power consumption is thus achieved.

According to the invention, the shafts of the solenoids can be arranged parallel and be connected to one another via a connector.

In a further embodiment of the invention, the connector itself serves as the pressure actuator. The connector can alternatively be connected to a pressure actuator.

In another embodiment of the invention the solenoids are arranged in series, with the shaft of the second solenoid being arranged such that it can influence the movement of the shaft of the first solenoid. A comparatively compact, space-saving choke valve is established as a result.

In another embodiment of the invention the solenoids are arranged in series and have a common shaft. The number of parts of the choke valve is thus reduced to a minimum.

BRIEF DESCRIPTION OF THE DRAWINGS

FIG. 1 is a schematic illustration of a first embodiment of a flow regulator according to the invention in a first position.

FIG. 2 shows the flow regulator of FIG. 1 in a second position.

FIG. 3 is a schematic illustration of a second embodiment of a flow regulator according to the invention.

FIG. 4 is a schematic illustration of a third embodiment of a flow regulator according to the invention.

FIG. 5 is a schematic illustration of a fourth embodiment of a flow regulator according to the invention.

DESCRIPTION OF THE PREFERRED EMBODIMENTS

Figure 6:
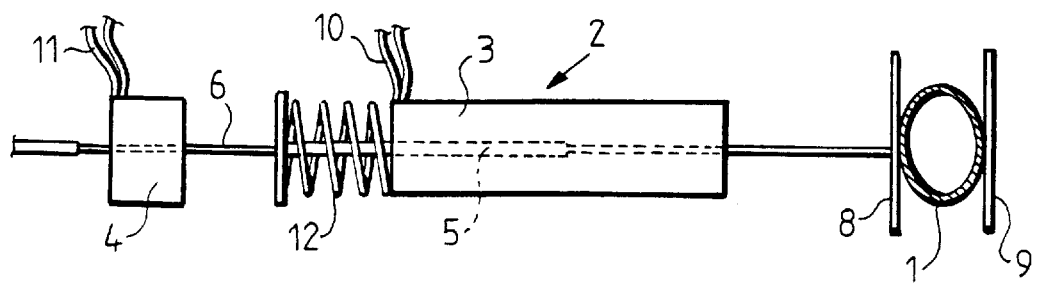
FIG. 6 is a schematic illustration of a fifth embodiment of a flow regulator according to the invention.

The flow regulator according to FIG. 1, which is preferably employed in combination with a respirator/ventilator (breathing assist device), has a conduit 1 (which may be the expiration line of the respiratory/ventilator) through which a medium flows whose flow is to be regulated, and a choke valve 2 arranged outside the conduit 1. The gas in the conduit 1 comes from a patient (not shown). The choke valve 2 has a first solenoid 3 and a second solenoid 4 that are arranged such that their respective shafts 5 and 6 proceed parallel and are connected to one another via a connector 7. The connector 7 is in turn connected to a pressure actuator 8. The choke 2 valve also has a fixed element 9, with the conduit 1 arranged between the fixed element 9 and the pressure actuator 8. The shafts 5 and 6 of the solenoids 3 and 4 are composed partly of a magnetic material and partly of a non-magnetic material. In all figures, the sections of the shafts 5 and 6 that are shown with a larger diameter are of a magnetic material. The first solenoid 3 is larger than the second solenoid 4 and also exhibits a significantly longer effective stroke length.

FIG. 1 shows that the common pressure actuator 8 of the solenoids 3 and 4 leaves the flow cross-section of the conduit 1 unaltered in a first limit position. By supplying more or less current to the solenoid 3 via lines 10, the part of the shaft 5 that is made of a magnetic material is influenced such that it is pushed out of the solenoid body to such an extent that the connector 7 causes the pressure actuator 8 to press against the conduit 1. The flow cross-section of the conduit 1 can be varied in this way, so that a desired gas flow is obtained. An example of such a position is shown in the Figure with the assistance of the dot-dash lines. Simultaneously with the displacement of the shaft 5, the shaft 6 of the second solenoid 4 is also passively displaced by the same path, so that the part of the shaft 6 that is made of a magnetic material approaches the solenoid body of the solenoid 4, this also being shown by doth-dash lines of the shaft 6. In this exemplary embodiment, the first solenoid 3 exhibits such an effective stroke length such that, with the assistance of the pressure actuator 8, it can completely compress the conduit 1 except for a few millimeters. Current is supplied to the solenoid 4 via lines 11 when the section of the shaft 6 that is made of magnetic material has reached the solenoid body. The shaft 6 of the solenoid 4, which exhibits an effective stroke length that corresponds to the distance required in order to completely compress the conduit 1, is now activated to exert such a force against the conduit 1 so that, as shown in FIG. 2, the conduit 1 is completely compressed. Since the solenoid 4 is dimensioned to be able by itself to generate a sufficient force against the conduit 1 to compress the conduit 1 completely against the fixed element 9, the current to the first solenoid 3 can be shut off, with the shaft 5 of the solenoid 3 being merely passively displaced over this final distance by the connector 7. During an inhalation phase, the solenoid 4 now holds the conduit 1 in a completely compressed position. During a following exhalation phase, the supply of current to the solenoid 4 is shut off, so that the shaft 6 thereof loses it force. A compression spring 12 retracts the shafts 5 and 6 and thus the pressure actuator 8 as well, into the originally described positions.

In the context of the invention, the first solenoid 3 can be dimensioned such that the effective stroke length of the shaft 5 suffices for completely compressing the conduit 1; however, it does not have sufficient force for such a compression. The second solenoid 4 can be dimensioned such that it cannot entirely compress the conduit 1 against the fixed element 9 by itself but the solenoids 3 and 4 in common can hold the conduit 1 in such a position during an inhalation phase.

FIG. 3 shows that said connector 7 described in conjunction with FIGS. 1 and 2 can itself serve as the pressure actuator.

FIGS. 4 and 5 show an embodiment wherein only the shaft 6 of the solenoid 4 is firmly connected to the pressure actuator 8. The flow regulator works in the same way as described in conjunction with FIGS. 1 and 2, with the difference that the power supply to the solenoid 3 is shut off after it is no longer needed. This means that, when the shaft 6 of the solenoid 4 or the pressure actuator 8, is activated in the described way to compress the conduit 1, the shaft 5 is returned into its original position by the compression spring 12. Such a position is shown in FIG. 5. When the power supply to the solenoid 4 is subsequently shut off, a compression spring 14 retracts the shaft 6 of this solenoid 4, and thus the pressure actuator 8 as well, back into their original positions, as shown in FIG. 4.

FIG. 6 shows that the solenoids 3 and 4 can be arranged in series instead in parallel, with the shaft 6 of the second solenoid 4 being arranged such that it can influence the shaft 5 of the first solenoid. Otherwise, the flow regulator works in the same way as described in conjunction with FIGS. 1 and 2. As a result of this structure, the pressure actuator 8 is detachably connected directly to the end face of the shaft 5.

Figure 7:
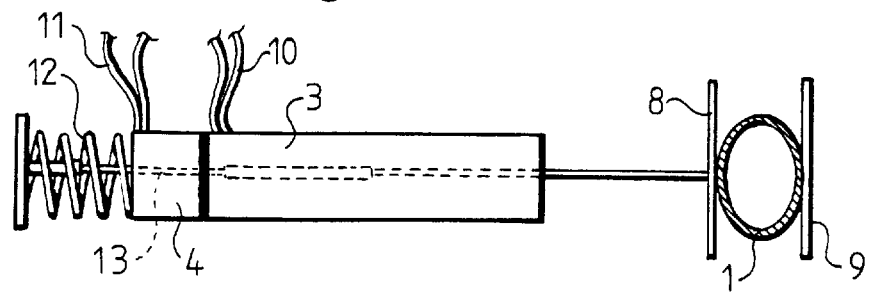
FIG. 7 is a schematic illustration of a sixth embodiment of a flow regulator according to the invention.

FIG. 7 shows that the series-arranged solenoids 3 and 4 can also have a common shaft 13.

The important advantage obtained by the invention is that, by employing two small solenoids with different effective stroke lengths, a flow regulator that is smaller, lighter and less expensive overall is established that uses comparatively little power and that, in particular, uses extremely little power when the smaller of the solenoids can exert a sufficient force against the conduit 1 by itself to compress the conduit 1 against the fixed element 9 such that the power supply to the larger of the two solenoids can be shut off.

Although modifications and changes may be suggested by those skilled in the art, it is the intention of the inventors to embody within the patent warranted hereon all changes and modifications as reasonably and properly come within the scope of their contribution to the art.

We claim as our invention:

1. A flow regulator comprising:

a compressible conduit through which a medium flows at a flow which is to be regulated;

a first solenoid having a first solenoid shaft;

a pressure actuator disposed at an end of said first solenoid shaft;

a fixed element, a portion of said compressible conduit being disposed between said pressure actuator and said fixed element;

said first solenoid having a first limit position at which said pressure actuator does not compress said compressible conduit and a second limit position at which said pressure actuator compresses said compressible conduit against said fixed element and thereby altering a cross-section of said portion of said compressible conduit while still permitting flow of said medium in said compressible conduit; and a second solenoid having a second solenoid shaft moveable through a stroke length which is less than a stroke length of said first solenoid shaft, said pressure actuator also being disposed at an end of said second solenoid shaft, and said second solenoid having a limit position at which said pressure actuator completely compresses said portion of said compressible conduit against said fixed element and entirely prevents flow of said medium through said compressible conduit.

2. A flow regulator as claimed in claim 1 wherein said first solenoid shaft and said second solenoid shaft are disposed parallel to each other, and further comprising a connector connecting said first solenoid shaft and said second solenoid shaft.

3. A flow regulator as claimed in claim 2 wherein said connector comprises said pressure actuator.

4. A flow regulator as claimed in claim 2 wherein said connector is also connected to said pressure actuator.

5. A flow regulator as claimed in claim 1 wherein said first solenoid and said second solenoid are disposed in series, with said second solenoid shaft disposed for influencing movement of said first solenoid shaft.

6. A flow regulator as claimed in claim 1 wherein said first solenoid and said second solenoid are disposed in series and have a common shaft comprising said first solenoid shaft and said second solenoid shaft.

7. A flow regulator as claimed in claim 1 wherein said first solenoid shaft and said second solenoid shaft are disposed parallel to each other, and wherein only said second solenoid shaft is directly connected to said pressure actuator.

8. A flow regulator as claimed in claim 1 wherein said second solenoid comprises means for displacing said pressure actuator with a force against said portion of said compressible conduit for, by itself, completely compressing said compressible conduit against said fixed element for entirely precluding flow of said medium through said compressible conduit.

* * * * *